(12) United States Patent
Galkin

(10) Patent No.: US 8,100,839 B2
(45) Date of Patent: *Jan. 24, 2012

(54) ACOUSTIC MONITORING OF A BREAST AND SOUND DATABASES FOR IMPROVED DETECTION OF BREAST CANCER

(76) Inventor: Benjamin M. Galkin, Cherry Hill, NJ (US)

(*) Notice: Subject to any disclaimer, the term of this patent is extended or adjusted under 35 U.S.C. 154(b) by 88 days.

This patent is subject to a terminal disclaimer.

(21) Appl. No.: 12/609,716

(22) Filed: Oct. 30, 2009

(65) Prior Publication Data

US 2010/0049093 A1 Feb. 25, 2010

Related U.S. Application Data

(63) Continuation-in-part of application No. 12/043,009, filed on Mar. 5, 2008, now Pat. No. 7,634,049, which is a continuation-in-part of application No. 11/752,142, filed on May 22, 2007, now Pat. No. 7,512,211, which is a continuation-in-part of application No. 11/279,280, filed on Apr. 11, 2006, now Pat. No. 7,248,668, application No. 12/609,716, which is a continuation-in-part of application No. 11/582,243, filed on Oct. 17, 2006, now Pat. No. 7,251,309, which is a continuation of application No. 11/246,419, filed on Oct. 7, 2005, now Pat. No. 7,142,631, which is a continuation-in-part of application No. 10/748,891, filed on Dec. 30, 2003, now Pat. No. 6,975,701.

(51) Int. Cl.
*A61B 7/00* (2006.01)
(52) U.S. Cl. ............ 600/586; 378/37
(58) Field of Classification Search ............ 378/37; 600/300, 437, 586
See application file for complete search history.

(56) References Cited

U.S. PATENT DOCUMENTS

| 4,529,635 A | 7/1985 | Sheldon |
| 4,691,333 A | 9/1987 | Gabriele et al. |
| 4,764,948 A | 8/1988 | Hurwitz |
| 4,962,515 A | 10/1990 | Kopans |
| 5,007,428 A * | 4/1991 | Watmough ............ 600/440 |

(Continued)

FOREIGN PATENT DOCUMENTS

DE 2335576 A1 1/1975

(Continued)

OTHER PUBLICATIONS

U.S. Appl. No. 60/187,198, filed Mar. 6, 2000, Lebovic et al.

(Continued)

*Primary Examiner* — Charles A Marmor, II
*Assistant Examiner* — Karen Toth
(74) *Attorney, Agent, or Firm* — Woodcock Washburn LLP

(57) ABSTRACT

Provided are methods and devices that pertain to the acquisition of data related to breast vascularity associated with breast cancer, use of data, or both, that are associated with the generation of sounds, including Korotkoff sounds, within a breast. The present methods and devices overcome the inherent limitations associated with x-ray absorption (upon which mammography relies) by the breast tissue of younger women, and may also be used to augment traditional single-parameter (visual) analysis of a breast through the use of a new parameter—sound. Also disclosed are databases comprising breast sounds that may be used to provide a more complete assessment of a patient's breast, either alone or in combination with the traditional visual parameter.

15 Claims, 7 Drawing Sheets

U.S. PATENT DOCUMENTS

| | | | |
|---|---|---|---|
| 5,063,583 | A | 11/1991 | Galkin |
| 5,199,056 | A | 3/1993 | Darrah |
| 5,276,726 | A | 1/1994 | Galkin |
| 5,311,883 | A | 5/1994 | Sherman |
| 5,377,254 | A | 12/1994 | Walling |
| 5,394,456 | A | 2/1995 | Livingston |
| 5,406,612 | A | 4/1995 | Galkin |
| 5,412,706 | A | 5/1995 | Deibel |
| 5,479,927 | A | 1/1996 | Shmulewitz |
| 5,506,877 | A | 4/1996 | Niklason et al. |
| 5,541,972 | A | 7/1996 | Anthony |
| 5,544,238 | A | 8/1996 | Galkin |
| 5,553,111 | A | 9/1996 | Moore et al. |
| 5,706,327 | A | 1/1998 | Adamkowski et al. |
| 6,049,583 | A | 4/2000 | Galkin |
| 6,122,542 | A | 9/2000 | Lee et al. |
| 6,333,970 | B1 | 12/2001 | LeMaitre et al. |
| 6,577,702 | B1 | 6/2003 | Lebovic et al. |
| 6,765,984 | B2 | 7/2004 | Higgins et al. |
| 6,850,590 | B2 | 2/2005 | Galkin |
| 6,928,139 | B2 | 8/2005 | Muller et al. |
| 6,968,033 | B2 | 11/2005 | Lebovic et al. |
| 6,969,033 | B2 | 11/2005 | Van der Linden |
| 6,974,255 | B1 | 12/2005 | Hixson, Sr. |
| 6,975,701 | B2 | 12/2005 | Galkin |
| 7,142,631 | B2 | 11/2006 | Galkin |
| 7,248,668 | B2 | 7/2007 | Galkin |
| 7,248,701 | B2 | 7/2007 | Gerrard et al. |
| 7,251,309 | B2 | 7/2007 | Galkin |
| 7,512,211 | B2 | 3/2009 | Galkin |
| 7,634,049 | B2 * | 12/2009 | Galkin ............... 378/37 |
| 2003/0007597 | A1 | 1/2003 | Higgins et al. |
| 2003/0058987 | A1 | 3/2003 | Rick et al. |
| 2003/0174807 | A1 | 9/2003 | Lebovic et al. |
| 2003/0194052 | A1 | 10/2003 | Price et al. |
| 2004/0081284 | A1 | 4/2004 | Livingston |
| 2005/0065418 | A1 * | 3/2005 | Ginor ............... 600/345 |
| 2005/0113683 | A1 | 5/2005 | Lokhandwalla et al. |
| 2005/0207528 | A1 | 9/2005 | Hijarn |
| 2006/0050844 | A1 | 3/2006 | Galkin |
| 2006/0258947 | A1 * | 11/2006 | Olson ............... 600/523 |
| 2008/0312514 | A1 * | 12/2008 | Mansfield ............... 600/300 |

FOREIGN PATENT DOCUMENTS

FR 2702059 A1 9/1994

OTHER PUBLICATIONS

Berns et al., "Effect of Foam Pads on Mammography Dose Calculation", Medical Physics, 45th Annual Meeting American Association of Physicists in Medicine, Aug. 10-14, 2003, 2 pages.

Brown, "Breast Cancer Diagnosis Often Delayed in Young Women", Reuters Health, Apr. 4, 2009.

Clark et al., "Pressure Measurements During Automatic Breast Compression in Mammography", J. Biomed Eng., 1990, 12(5), pp. 444-446.

Fenton et al., New England Journal of Medicine, Apr. 5, 2007, 356(14), pp. 1399-1409.

Galkin et al., "The Breast Pillow™: A Novel Device to Reduce Patient Discomfort and Pain During Mammography While Also Measuring Compression Force(1)", Med. Physics, Aug. 2001, 28(8), SU-HH-EXH C-10, 1 page.

Galkin et al., "The Breast Pillow™: A Novel Device to Reduce Patient Discomfort and Pain During Mammography While Also Measuring Compression Force", Poster Exhibit presented at the annual meeting of the American Association of Physicists in Medicine, Jul. 22-26, 2001, Abstract SU-HH-EXH C-10 published in Med. Phys., 2001, p. 1820.

Galkin et al., "The Breast Pillow™; A Mammography Device for Reducing Patient Discomfort and Pain", 2001, 0768BR-c, 1 page.

Galkin et al., "The Breast Pillow™; A Mammography Device for Reducing Patient Discomfort and Pain", Education exhibit presented at the annual meeting of the Radiological Society of North America, Nov. 25-30, 2001, Abstract 0768BR-e published in Supplement to Radiology, 2001, 221 (P), p. 68.

Heath et al., "The Digital Database for Screening Mammography", The Proceedings of the 5th International Workshop on Digital Mammography, Jun. 2000.

Keshavmurthy et al., "Design and Evaluation of an External Filter Technique for Exposure Equalization in Mammography", Medical Physics, Aug. 1999, 26(8), pp. 1655-1669.

Kruger et al., "Light Equalization Radiography", Medical Physics, Jul./Aug. 1990, 17(4), pp. 696-700.

Lam et al., "Effects of X-Ray Beam Equalization on Mammographic Imaging", Medical Physics, Mar./Apr. 1990, 17(2), pp. 242-249.

Lam et al., "Exposure Equalization Technique in Mammography", Investigative Radiology, 1989, pp. 154-157.

Panayiotakis et al., "An Anatomical Filter for Exposure Equalization in Mammography", European Journal of Radiology, Jul.-Aug. 1992, vol. 15, Issue 1, pp. 15-17.

Plewes et al., "Role of Equalisation Mammography of Dense Breasts", Medical & Biological Engineering & Computing, Mar. 1995, pp. 167-173.

S.O.F.T. Paddle® by American Mammographics, http://www.americanmammographics.com/SOFTPaddle.htm, Dec. 2002, 2 pages.

Saab, "Applications of High-Pressure Balloons in the Medical Device Industry", 1999, Advanced Polymers, Inc., http://www.advpoly.com/NewsData/BalloonPaper.pdf, 19 pages.

Sabol et al., "A Method for Pratical Equalization Mammography of the Radiographically Dense Breast", Imaging and Therapeutic Technology, 1995, 15(5), 1191-1202.

Sabol et al., "Mammographic Scanning Equalization Radiography", Medical Physics, Sep./Oct. 1993, 20(5), 1505-1515.

Vyborny et al., "Folil Filters for Equalized Chest Radiography", Radiology, 1984, p. 524.

* cited by examiner

FIG. 4
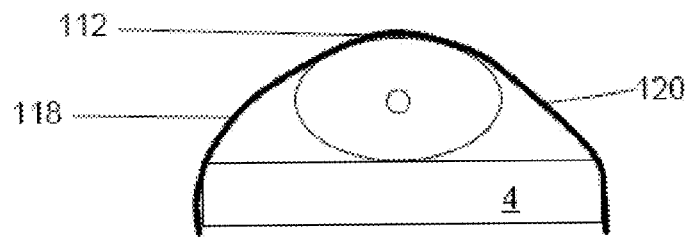
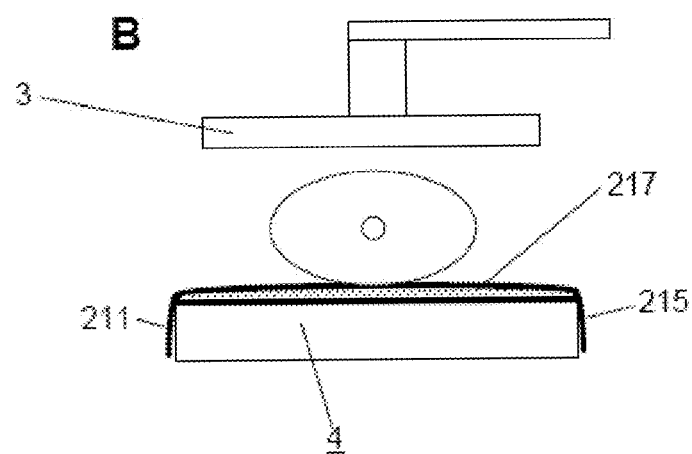
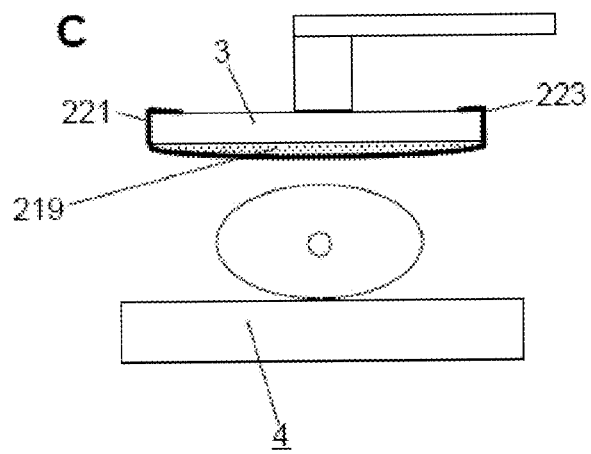

FIG. 5
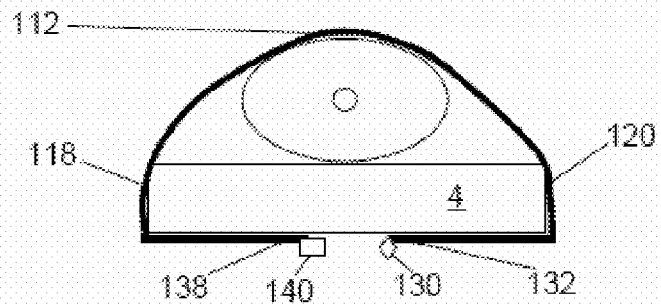
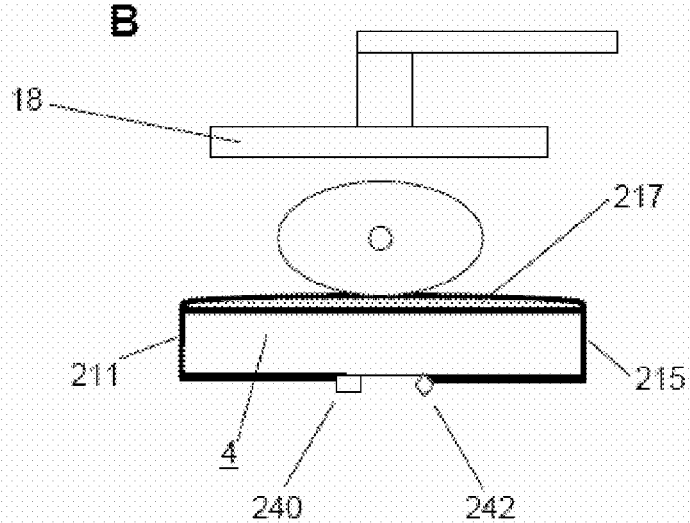
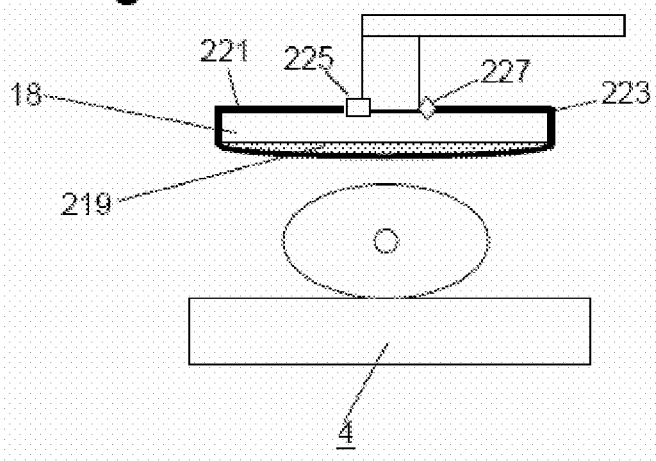

FIG. 7
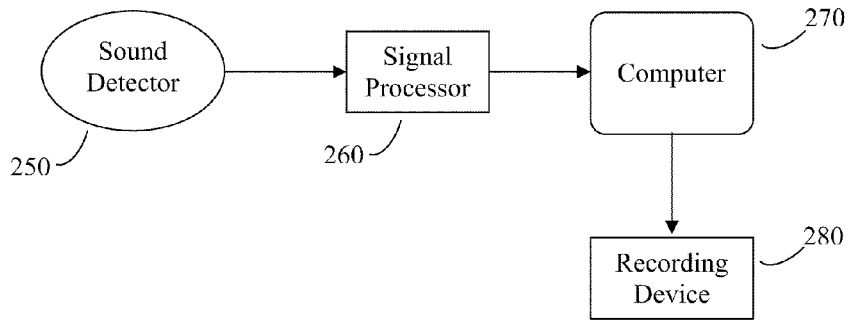
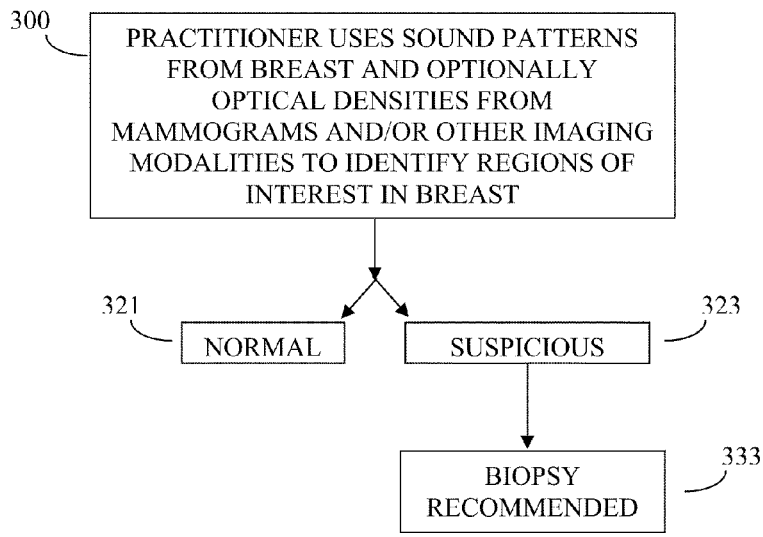
FIG. 8
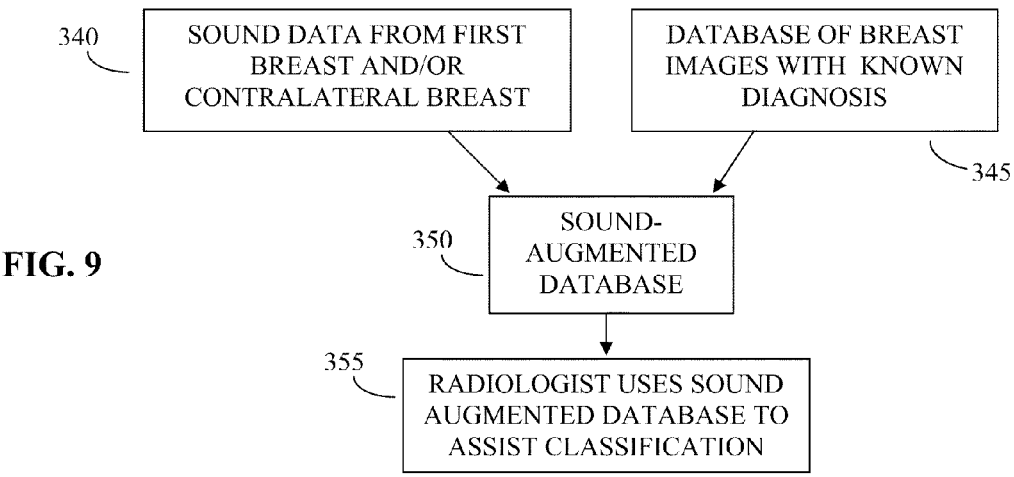
FIG. 9

ACOUSTIC MONITORING OF A BREAST AND SOUND DATABASES FOR IMPROVED DETECTION OF BREAST CANCER

CROSS REFERENCE TO RELATED APPLICATIONS

This application is a continuation-in-part of U.S. Ser. No. 12/043,009, filed Mar. 5, 2008, now U.S. Pat. No. 7,634,049 which is a continuation-in-part of U.S. Ser. No. 11/752,142, filed May 22, 2007 (now U.S. Pat. No. 7,512,211), which is a continuation-in-part of U.S. Ser. No. 11/279,280, filed Apr. 11, 2006 (now U.S. Pat. No. 7,248,668) and a continuation-in-part of U.S. Ser. No. 11/582,243, filed Oct. 17, 2006 (now U.S. Pat. No. 7,251,309), which is a continuation of U.S. Ser. No. 11/246,419, filed Oct. 7, 2005 (now U.S. Pat. No. 7,142,631), which is a continuation-in-part of U.S. Ser. No. 10/748,891, filed Dec. 30, 2003 (now U.S. Pat. No. 6,975,701). Each of the applications listed above is herein incorporated by reference in its entirety.

TECHNICAL FIELD

The present inventions relate to the field of mammography, and more specifically to methods and systems that utilize breast sounds pursuant to screening for breast cancer.

BACKGROUND

Mammography is the process of obtaining x-ray images of the human breast for diagnosis or surgery. It involves positioning a patient's breast in a desired orientation against a cassette holder (also known as a "bucky") of a mammography unit, compressing the breast with a compression device (e.g., a compression paddle), and then exposing the breast to x-rays to create a latent image of the breast on an image receptor. After exposure, the compression device is released.

Typically, the compression device is a compression paddle, which includes a rectangular flat plate that is attached to the mammography unit between an x-ray tube assembly and the bucky. The edges of the paddle are usually turned upward away from the bucky to provide a smooth curved surface for patient comfort. The compression paddle is usually made of thin, light-transparent, plastic that absorbs only a small fraction of the incident x-ray beam. The compression paddle is moved either manually or by power drive to apply a compression force to the breast, thereby limiting breast motion and flattening the breast against the cassette holder to a near uniform thickness to improve image quality. U.S. Pat. No. 6,049,583 issued to the present inventor discusses methods and apparatus for measuring compression force in mammography. During compression, parts of the patient's body come into contact with the compression paddle. After x-ray exposure, the compression force is released for patient comfort.

Angiogenesis plays an important role in the development of breast carcinoma. The use of contrast and molecular imaging agents to detect and/or treat breast cancer also relies on breast vascularity. Unfortunately, traditional mammography systems that exert static compression force on a breast that is positioned between a bucky and a compression paddle are incompatible with studies relating to blood flow during mammography screening, as the static compression force at least partially interrupts blood flow within the breast.

There have been increasing efforts among medical practitioners, analysts, and statisticians to create databases that include compilations of information relating to observation, assessment, and treatment of patient findings, and that permit physicians to refer to such information while performing a diagnosis or selecting an appropriate therapy regimen. Examples are the American College of Radiology (ACR) Breast Imaging Reporting and Data System Atlas (BI-RADS® Atlas) and their National Mammography Database (NMD).

However, recent studies have revealed that although mammograms are not typically recommended for women under the age of 40 (at least partly because the density of the breasts of such women are thought to interfere with the accuracy of mammograms, which rely on variations in tissue density to aid in the detection of possible tumors), the vast majority of breast cancers in young women would have been detectable with mammography, MRI, or both, yet in most cases, imaging was not performed prior to diagnosis. See Brown, Anthony J., MD, *Breast Cancer Diagnosis Often Delayed in Young Women, Reuters Health*, Apr. 4, 2009. Thus, traditional mammograms and databases that include information pertaining to this and other traditional methodologies do not address the inherent limitations of mammograms in younger women. Furthermore, mammograms, MRI, and ultrasound each constitute relatively costly measures for obtaining a routine diagnosis of breast health. Especially under any new health care regime such as that currently under debate among American legislators, low-cost measures for effectively diagnosing patient health would be highly regarded.

There remains a need for further systems, techniques, and databases that permit the study of breast vascularity pursuant to a cost-effective assessment of breast health among women of all ages.

SUMMARY

Provided are methods and devices that pertain to the acquisition of data, use of data, or both, that are associated with the generation of sounds, including Korotkoff sounds, within the breast. The present methods and devices effectively overcome the inherent limitations associated with the assessment of x-ray absorption (upon which mammograms rely) by the breast tissue of younger women, and represent a low-cost and repeatable means for screening for vascular abnormalities in the breast. Numerous other advantages are provided by the disclosed inventions and are discussed more fully herein.

In one aspect, there are disclosed methods comprising: (a) securing a first compression device comprising an inflatable chamber over a surface of a first breast of a patient positioned on a support surface; (b) at least partially filling the inflatable chamber of the compression device with a fluid, thereby compressing the breast between the inflatable chamber and the support surface and at least partially occluding blood flow to the breast; (c) releasing at least a portion of the fluid from the inflatable chamber, wherein the release of the fluid from the chamber controls the resumption of blood flow to the breast; (d) detecting sounds generated by the resumption of blood flow to the breast; (e) repeating each of the steps (a)-(d) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

In another aspect, there are provided methods comprising (a) securing a first compression device comprising an inflatable chamber over a support surface, so that when a first breast of a patient is positioned upon the support surface, the breast is interposed between the first compression device and a compression surface positioned above a upper surface of the breast; (b) at least partially filling the inflatable chamber of the first compression device with a fluid, thereby compressing the breast between the inflatable chamber and the compression surface and at least partially occluding blood flow to the breast; (c) releasing at least a portion of the fluid from the inflatable chamber, wherein the release of the fluid from the chamber controls the resumption of blood flow to the breast; (d) detecting sounds generated by the resumption of blood flow to the breast; (e) repeating each of the steps (a)-(d) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

Also disclosed are methods comprising (a) securing a first compression device comprising an inflatable chamber to a compression paddle; (b) at least partially filling the inflatable chamber of the first compression device with a fluid, thereby compressing a first breast of a patient that is positioned on a support surface between the inflatable chamber and the support surface, and at least partially occluding blood flow to the breast; (c) releasing at least a portion of the fluid from the inflatable chamber, wherein the release of the fluid from the chamber controls the resumption of blood flow to the breast; (d) detecting sounds generated by the resumption of blood flow to the breast; (e) repeating each of steps (a)-(d) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

In another aspect, there are disclosed methods comprising (a) compressing a first breast of a patient, whereby the resulting compression occludes at least some blood flow to the breast; (b) at least partially relieving such compression, such that blood flow to the breast is at least partially restored; (c) detecting Korotkoff sounds within the breast; (d) repeating each of steps (a)-(c) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

In yet another aspect there are disclosed methods comprising using a comparison of data derived from the detection of Korotkoff sounds within a patient's first breast and data derived from the detection of Korotkoff sounds within a patient's contralateral breast to perform a diagnosis relating to the presence or absence of a disease or condition in the patient, the stage of the disease or condition in the patient, or the response of the disease or condition in the patient to a therapy regimen.

Also disclosed are apparatuses comprising a support surface that is configured for accommodating a breast of a patient; a first compression device comprising an inflatable chamber, wherein the first compression device may be secured over a surface of the breast while positioned on the support surface, and wherein when the inflatable chamber is at least partially inflated by at least partially filling the inflatable chamber of the first compression device with a fluid, the breast is compressed between the inflatable chamber and the support surface and blood flow to the breast is at least partially occluded; and, a sound detector for detecting Korotkoff sounds that are generated within the breast when the compression of the breast is at least partially relieved, such that blood flow to the breast is at least partially restored.

In another aspect, there are provided apparatuses comprising a support surface that is configured for accommodating a breast of a patient; a first compression device comprising an inflatable chamber that is secured to the support surface; a compression surface that may be positioned above a upper surface of the breast such that the breast is interposed between the first compression device and the compression surface; wherein when the inflatable chamber is at least partially inflated by at least partially filling the inflatable chamber of the first compression device with a fluid, the breast is compressed between the inflatable chamber and the compression surface and blood flow to the breast is at least partially occluded, and, a sound detector for detecting Korotkoff sounds that are generated within the breast when the compression of the breast is at least partially relieved, such that blood flow to the breast is at least partially restored.

In yet another aspect, there are provided apparatuses comprising a support surface that is configured for accommodating a breast of a patient; a compression surface that may be positioned above a upper surface of the breast such that the breast is interposed between the first compression device and the compression surface; a first compression device comprising an inflatable chamber that is secured to the compression surface; wherein when the inflatable chamber is at least partially inflated by at least partially filling the inflatable chamber of the first compression device with a fluid, the breast is compressed between the inflatable chamber and the support surface and blood flow to the breast is at least partially occluded, and, a sound detector for detecting Korotkoff sounds that are generated within the breast when the compression of the breast is at least partially relieved, such that blood flow to the breast is at least partially restored.

Another aspect of the present invention is a database comprising data corresponding to a sound from at least one breast. The sound may be a Korotkoff sound.

BRIEF DESCRIPTION OF THE DRAWINGS

The present invention will be better understood, and its numerous objects and advantages will become apparent to those skilled in the art by reference to the following detailed description when taken in conjunction with the following drawings, in which:

FIGS. 4A-4C provide front views of embodiments of compression devices that are secured over the top of a breast to the support surface, secured directly over a support surface, and secured to a compression surface, respectively.

FIGS. 5A-5C provide front views of other embodiments of compression devices that are secured over the top of a breast to the support surface, secured directly over a support surface, and secured to a compression surface, respectively.

FIG. 7 is a schematic of one possible arrangement among components that may be used to detect, store, and process sound information from within a patient's breast.

FIG. 8 depicts a sound detection procedure in accordance with another embodiment of the present invention.

FIG. 9 illustrates how an image database may be enhanced by use of sound data in accordance with the present invention.

DETAILED DESCRIPTION OF ILLUSTRATIVE EMBODIMENTS

Figure 1:
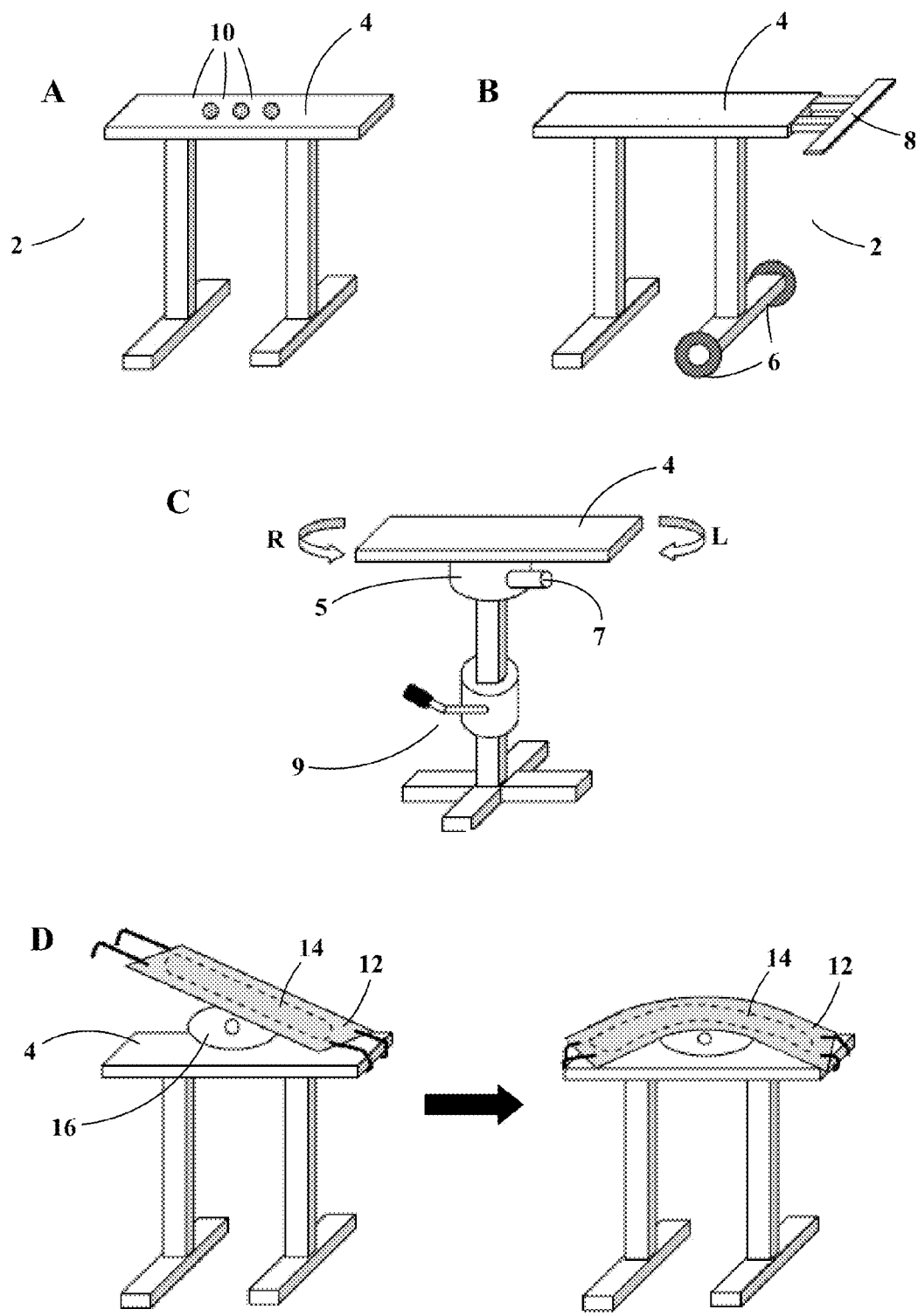
FIG. 1 depicts various exemplary embodiments of the present apparatuses including a support surface and at least one compression device for compressing and at least partially releasing pressure on a breast in order to generate Korotkoff sounds.

Provided are methods and devices that pertain to the acquisition of data, use of data, or both, that are associated with the generation of Korotkoff sounds within the breast.

The instant methods and apparatuses involve the compression of the subject breast (a first breast or a second, contralateral breast) against a support surface, against a surface above an upper surface of the breast, or both, preferably outside of the context of a traditional mammography unit, in order to at least partially occlude the flow of blood to the breast such that Korotkoff sounds can be detected from within the breast once the flow of blood to the breast is resumed. The devices comprise at least one inflatable chamber for containing a fluid, for example, a pressurized gas. Inflatable chambers can be, for example, medically acceptable balloons. When fluid is introduced into the chamber, at least one surface of the chamber expands. The expansion may be in the direction of the support surface, or may be in the opposite direction, depending on the placement of the device, as described herein.

For example, in one embodiment, the devices secure the breast to a support surface by wrapping over the top or upper surface of the breast. The compression devices are preferably adapted for being secured over the upper surface of the breast, i.e., include features that permit the compression device to be secured over the upper surface of the breast. For example, side flaps, cords, straps, or any other suitable feature can be used to secure the device to and/or around the support surface. Generally, when in position over the breast (and not inflated), the inflatable chamber partially conforms to the shape of the breast. Compressed air, for example, can be introduced, manually or automatically, to inflate the chamber. As the chamber expands, breast motion is limited and the breast is compressed against the surface of the support surface. Inflation of the chamber can at least partially occlude blood flow in the breast. The support surface in accordance with any embodiment of the present invention may be any surface on which a breast or pair of breasts can be placed at a resting state. Everyday surfaces such as the top of an examining table can suffice, although surfaces that are specifically configured in terms of size, shape, and/or height may also be used. For example, the support surface may be the upper surface of a stand or wheeled platform that is appropriately proportioned for accommodating a breast or a pair of breasts of a patient. Such stands and wheeled platforms are described more fully herein. In other embodiments, the support surface may be integrated into a mammography unit, for example, such that the bucky of the mammography unit may serve the dual purpose of being a support surface in accordance with the present disclosure. When the support surface is integrated into a mammography unit, use of the support surface as described herein may be temporally separate and distinct from the mammography process.

In another embodiment, the compression devices comprise an inflatable chamber that is interposed between the breast and the support surface. These compression devices may be referred to as being located on the underside of a breast, and are positioned at the side of the breast that is proximal to the support surface. Such compression devices are preferably adapted to secure the device on top of the support surface, i.e., include features that permit the compression device to be secured over the support surface. For example, side flaps, cords, straps, or any other suitable feature can be used to secure the device to and/or around the support surface. Fluid can be introduced to inflate the chamber, and when an additional compression surface (e.g., a paddle) or an inflatable chamber device in accordance with the preceding embodiment (i.e., a device that is wrapped over the upper surface of the breast) is positioned over the breast, the inflation of the chamber can compress the breast against the paddle or device positioned above the upper surface of the breast. Here, too, inflation of the chamber can at least partially occlude blood flow in the breast.

Traditional mammography units employ a compression paddle, which includes a rectangular flat plate that is attached to the mammography unit between an x-ray tube assembly and the bucky. The compression devices of the instant invention can comprise an inflatable chamber that is secured to the underside of a similar type of paddle or paddle-like component in the form of a compression surface that may or may not be associated with a mammography system. Such compression devices are herein referred to as those that are mounted on or secured to a compression surface. For example, side flaps, cords, straps, or any other suitable feature can be used to secure the device to and/or around the compression surface. Generally, when in position over the breast (and not inflated), the inflatable chamber partially conforms to the shape of the breast. Compressed air, for example, can be introduced, manually or automatically, to inflate the chamber. As the chamber expands, breast motion is limited and the breast is compressed against the support surface. Inflation of the chamber can at least partially occlude blood flow in the breast.

The apparatuses and methods according to the present invention may therefore provide a compression device that is located above the upper surface of a breast that is positioned on a support surface, a compression device that is positioned below the bottom surface of a breast, a compression device that is mounted on a compression surface, or may comprise any combination of such configurations, such as both a compression device that is located above the upper surface of a breast and a compression device that is positioned below the bottom surface of a breast.

In each of these embodiments, fluid may be released from the chamber(s) via a valve or some other outlet means, and as the chamber(s) is at least partially deflated, blood flow is restored to the breast, producing Korotkoff sounds that may be detected by a sound detection device. The sounds are collected from the entire breast and/or selected regions of interest. A comparison of sound patterns from both breasts can provide an objective metric that may be used in conjunction with a CAD process and/or a database of mammograms having validated diagnosis.

In 1905, Dr. Nikolai Korotkoff reported that turbulence in blood flow in vivo can produce audible sounds. These sounds are now routinely used to measure blood pressure, typically through use of a stethoscope in conjunction with a blood pressure gauge (sphygmomanometer). However, the detection of Korotkoff sounds within a breast has never been used or proposed for use in assessing the presence or absence of a disease or condition in a patient, assessing the stage of a disease or condition in a patient, or assessing the response of a disease or condition in a patient to a therapy regimen. The instant invention involves the use of Korotkoff sounds to generate useful data concerning the vascularity of the subject breast. Angiogenesis plays an important role in the development of breast carcinoma, and information concerning the vascularity of a patient's breast can improve the diagnostic process. Furthermore, this information could be useful in differentiating between benign and malignant breast conditions prior to biopsy. Currently, it is known that the increased rate of biopsy that has resulted from the use of CAD is not clearly associated with improved detection of invasive breast cancer (Fenton J J et al., *N Engl J Med.* 2007 Apr. 5; 356(14): 1399-409) and the introduction of a new data parameter could reduce the incidence of unnecessary biopsies.

In addition, in view of the fact that a standard breast checkup may include the examination of both breasts of a patient, the instant invention may involve the detection of sounds, including Korotkoff sounds, from both a first breast of a patient and the contralateral breast of a patient. Sound data from both breasts may be used to enhance the diagnostic process, for example, by permitting a comparison between the data from a first breast to the data from the contralateral breast; it is frequently the case that a breast condition is present in only one of a patient's breasts, and a difference between the data obtained from a patient's respective breasts can alert a practitioner to the possibility that one of the breasts should be subjected to further examination. The data obtained from a patient's respective breasts may also or alternatively be used, for example, to enhance a computer-aided detection (CAD) program; to aid in an analysis of a mammogram; to aid in the analysis of the results of an MRI of a breast; to aid in the analysis of the results of an ultrasound of a breast; in conjunction with the use of a database of mammography images; to form or contribute to a database of breast sounds; in conjunction with the use of a database of sounds from breasts of patients in which a disease or condition was known to be absent, known to be present, or both; or any combination thereof.

For example, if an region of interest is identified in a first breast by a CAD program (e.g., by the identification of a location in the image of a breast having a certain pixel value, corresponding to a higher than average optical density), sound data from the region of interest in the first breast may be obtained and compared with sound data from the corresponding anatomical region of interest in the second breast; if the comparison indicates a significant difference between the acoustic properties in the region of interest in the first breast and the acoustic properties in the corresponding area in the second breast, such findings may buttress the findings of the CAD program, and thereby alert the practitioner and/or warrant additional studies. Alternatively, if the difference between the sound data from the first breast and the sound data from the contralateral breast is within a certain range of tolerance, then the practitioner could have reason to suspect that the region of interest as designated by the CAD program is not the site of a malignant growth. It is well known that the blood flow properties, caused, for example, by differences in blood vessel diameter and growth density, are different in cancerous tissue than in normal tissue.

Additionally or alternatively, sound data from a first breast of a patient, from a contralateral breast of a patient, or both, may be used—in isolation from a mammographic, MRI, or ultrasound analysis—to provide an assessment as to the presence or absence of said disease or condition in the patient, the stage of a disease or condition in the patient, or the response of a disease or condition in the patient to a therapy regimen. For example, sound data from a first breast, a contralateral breast, or both, may be acquired from a patient, and then compared to comparable sound data from one or more subjects in which a disease or condition was known to be absent, to comparable sound data from one or more subjects in which a disease or condition was known to be present, or to both, and the comparison may be correlated to the presence or absence of the disease or condition in the patient, to the stage of the disease or condition in the patient, or to the response of the disease or condition in the patient to a therapy regimen. The present methods and devices overcome the inherent limitations associated with the assessment of x-ray absorption (upon which mammography relies) by the breast tissue of younger women. Therefore, the present methods and devices may be used in connection with female subjects that are of any age, including subjects that are 40 years old or younger, or that are 30 years old or younger. Furthermore, the present methods and devices represent a low-cost and repeatable means for screening for vascular abnormalities in the breast. Although the acquisition and analysis of sound data may initially be separate from a mammogram, an MRI, an ultrasound, molecular imaging, elastography, or any other type of analysis of a breast, the sound data may subsequently be used to aid in the interpretation of a mammogram, an MRI, an ultrasound, the results of molecular imaging, an elastographic analysis, etc. Sound data may provide a quantitative metric that can be used to enhance the usefulness of a database of breast images, such as one including data from mammograms, MRI, ultrasound, results of molecular imaging, elastographic analysis, or any other visual data regarding a breast.

As depicted in FIG. 9, breast sound data 340 from one or more subjects may be used to augment 350 a database of breast images 345. Accordingly, whereas existing databases may provide a single parameter for use in assessing a patient's breast (e.g., a visual image), image databases that have been augmented with sound data in accordance with the present invention provide two parameters (image data and sound data) that may be considered during the assessment of a patient's breast 355. The integration of sound data with image data preferably involves the matching of images from known conditions or structures with sounds that are known to correlate to the same conditions or structures. Thus, a practitioner may acquire image and sound data from a patient's breast, and then consult a combined image/sound database according to the present invention in order to compare the acquired image data from the patient's breast to image data from the database, and compare the acquired sound data from the patient's breast to sound data from the database. A database according to the present disclosure that comprises sound data, or both sound data and image data, may be electronically stored and made remotely or otherwise electronically accessible to practitioners. "Image data" according to the present invention may be from a mammogram, an MRI, an ultrasound, molecular imaging, elastography, or any other modality for the visual analysis of a breast.

Thus, unlike prior methods, the present invention exploits the sounds created by the blood flow properties of a tissue (such as a region of interest) within a breast or the global blood flow properties of a breast, as well as a comparison with corresponding properties in a contralateral breast, in order to obtain valuable additional data parameters regarding the physiological characteristics of a patient's breasts.

The compression devices of the present invention comprise one or more inflatable chambers. Inflatable chambers increase in volume when pressurized fluid is introduced. A medically acceptable balloon is an example of an inflatable chamber. Chambers used in embodiments of the present invention can be, for example, high pressure balloons. High pressure balloons are used in various applications in the medical industry, such as in angioplasty. See Saab, *Applications of High-Pressure Balloons in the Medical Device Industry*, http://www.advpoly.com/NewsData/BalloonPaper.pdf (http://www.devicelink.com/mddi/archive/00/09/003.html).

A manifold may be operatively associated with the inflatable chamber for introducing a fluid into the inflatable chamber and/or for receiving the fluid from the inflatable chamber. In some embodiments, a source of compressed air that is in fluid communication with the manifold is provided.

In certain embodiments, the compression device comprises multiple inflatable chambers. For example, a second inflatable chamber can be used to help distribute the compression force exerted against the breast. The shape of the chambers can vary as needed. In the present disclosure, recitation of "a component" can mean at least one of such components. More generally, in the present disclosure the singular forms "a," "an," and "the" include the plural reference, and reference to a particular numerical value includes at least that particular value, unless the context clearly indicates otherwise. Thus, for example, a reference to "a sound detector" is a reference to one or more of such sound detectors and equivalents thereof known to those skilled in the art, and so forth. For purposes of the present disclosure, all references to devices or methods in which "a breast" or "the breast" is analyzed are intended to embrace the analysis of one breast of a patient or both breasts of the patient. For example, it is intended that any method that is described with respect to a breast of a patient is applicable to the other breast of a patient, and any method steps recited therein with respect to one breast may be repeated in connection with the second breast of the patient. Furthermore, it is preferred that such method steps are performed separately with respect to each breast; for example, the step of "detecting sounds within the first breast and within the contralateral breast when such breasts are not compressed" means that the detection of sounds within the first breast is performed in an episode that is separate but identical to the detection of sounds within the contralateral breast.

As used herein, a "sound detector" is any device that is capable of detecting those sounds that are produced by the flow of blood within tissue, such as a subject breast. For example, any device that functions comparably with a stethoscope may be used. Electronic sound detectors include sensors that may be taped to the outer surface of patient skin at particular locations, may be affixed proximate to the inflatable chamber of a compression device, or may be integrated with one or more other components of the present apparatuses. When affixed proximate to the inflatable chamber of a compression device, the sound detectors are ideally placed in fluid communication with such inflatable chamber, so that Korotkoff sounds can travel from their locus of origin within the breast to the sound detector via the inflatable chamber, and such configuration works best when the inflatable chamber is at least partially filled with fluid. In instances where one or more sound detectors are integrated with a component of the apparatus, a sound detector may, for example, be located at the surface of or within the support surface, an inflatable chamber, or a compression surface. The sounds that are detected pursuant to the present invention may be within the normal range of human hearing, or may be above or below the normal range of human hearing. For example, the sounds may be outside of the normal range of human hearing but detectable by a sound detector and capable of being recorded.

Preferably, the sound detector is adapted to generate an electrical signal that can be converted to a frequency domain signal that can in turn be digitized for computer storage. More preferably, the sound detector is adapted to permit transfer of the detected sound information to a separate device that can convert the detected sound information to a frequency domain signal that can be digitized for computer storage. Frequency domain signal conversion and digitization are processes that are widely understood by those skilled in the art, and the skilled artisan will readily appreciate how a sound detector may be adapted for use with such processes.

Preferably, the sound detectors can be activated at any time during the compression process. For example, sound detectors can be used to detect sounds from within a breast prior to compression by an inflatable chamber, during compression by an inflatable chamber, as compression by an inflatable chamber is being relieved by partial deflation of the inflatable chamber, and/or after compression of the breast has been fully relieved.

Sounds that are ascertained by the sound detector and converted to recordable data can subsequently be used to form or contribute to a database of sounds, or may otherwise be compared with libraries of sounds from known cases of cancer, for example, to determine the probability of malignancy. As used herein, a "sound database", "database of sounds", "library of sounds", and the like may include databases of acoustic information, whether such information is digitized or analog, or whether the acoustic information is a recording of one or more sounds, one or more portions of a sound, or one or more characteristics of a sound; or, is a graphical depiction of one or more sounds, one or more portions of a sound, or one or more characteristics of a sound. Unless otherwise specified, the term "sound" may refer to a sound, one or more portions of a sound, or one or more characteristics of a sound. Because the present disclosure is the first to teach the use of breast sounds to form a database of sounds, any comparison of acquired sounds to a database of breast sounds must obviously be preceded by the formation of such a database in accordance with the procedures described by the present disclosure. A clinician can also correlate Korotkoff sound data with the information regarding visual mammography features stored in the Digital Database for Screening Mammography ("DDSM"). The DDSM is a publicly available library of features observed on mammograms that can be used as a reference during the diagnostic process. See Heath M et al., "*The Digital Database for Screening Mammography*", in *The Proceedings of the 5th Int'l Workshop on Digital Mammography* (Toronto, Canada, June 2000), *Medical Physics Publishing* (Madison, Wis.). As used herein, a "mammography database" may include databases of mammography images, whether such images are digitized or analog.

The comparison of the sound data from the respective breasts of a patient can be used to generate a metric, for example, a ratio, that can be evaluated in the light of comparable data from subjects in which an abnormal condition was known to be absent, known to be present, or both. In other words, comparison of a such a metric with information from a database can provide the diagnostician with information pertaining to the condition of one or both of the patient's breasts.

With respect to any of the methods of the present invention, the detected sounds from the first breast and the contralateral breast of the patient may each be converted to an acceptable data format, such as a frequency domain signal, and the sound data corresponding to the first breast may be compared to the sound data corresponding to the contralateral breast. The comparison may provide a comparison metric, and the resulting metric may be used in connection with a CAD process, a mammogram analysis, a comparison with sound database records, or any combination thereof.

A compression surface according to the present invention can be a traditional paddle or can be a compression device positioned above the top or upper side of a breast as described previously. When the compression surface is a paddle, a paddle-mounted compression device comprising an inflatable chamber can be secured thereto; the paddle-mounted compression device can also be at least partially filled with a fluid and used to compress the breast between itself and a compression device secured to the support surface, or between itself and the support surface alone.

A compression surface may include a flat plate, preferably having edges of that are turned upward away from the support surface to provide a smooth, curved surface for patient comfort. The surface may be any appropriate shape, such as rectangular, square, substantially round, or substantially oval. The compression surface may be made of thin, light-transparent, plastic, may be made of metal, or may be made of any material that can withstand the force necessary to compress a breast without breakage or excessive deflection.

In embodiments wherein the compression surface is moved in order to effect compression of a breast (by itself or in combination with the inflation of a compression device that is mounted on the compression surface or that is mounted on the support surface), the compression paddle is moved either manually or by power drive to apply a compression force, thereby limiting breast motion and flattening the breast against the support surface or against a compression device that is mounted on the support surface, preferably to a near uniform thickness. U.S. Pat. No. 6,049,583 issued to the present inventor discusses methods and apparatus for measuring compression force in mammography, which is relevant by analogy to the present methods and apparatuses.

The inventive methods can include (a) securing a first compression device comprising an inflatable chamber over a surface of a first breast of a patient positioned on a support surface; (b) at least partially filling the inflatable chamber of the compression device with a fluid, thereby compressing the breast between the inflatable chamber and the support surface and at least partially occluding blood flow to the breast; (c) releasing at least a portion of the fluid from the inflatable chamber, wherein the release of the fluid from the chamber controls the resumption of blood flow to the breast; (d) detecting sounds generated by the resumption of blood flow to the breast; (e) repeating each of the steps (a)-(d) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

Such methods may further comprise securing a second compression device comprising an inflatable chamber over the support surface, and at least partially filling the inflatable chamber of the second compression device with a fluid, thereby compressing the first breast and the contralateral breast, respectively, between the inflatable chamber of the second compression device and the first compression device. In other words, whether the first breast and the contralateral breast are compressed simultaneously or in sequence (i.e., one breast is compressed and at least partially released, and then the other breast is compressed and at least partially released), the compression of one or both breasts may be compressed between the second compression device and the first compression device. In order to generate Korotkoff sounds, at least a portion of the fluid from the inflatable chamber of the first compression device, from the inflatable chamber of the second compression device, or both, may be released, and sounds that are generated by the resumption of blood flow to one or both breasts may be detected.

In another aspect, there are provided methods comprising (a) securing a first compression device comprising an inflatable chamber over a support surface, so that when a first breast of a patient is positioned upon the support surface, the breast is interposed between the first compression device and a compression surface positioned above a upper surface of the breast; (b) at least partially filling the inflatable chamber of the first compression device with a fluid, thereby compressing the breast between the inflatable chamber and the compression surface and at least partially occluding blood flow to the breast; (c) releasing at least a portion of the fluid from the inflatable chamber, wherein the release of the fluid from the chamber controls the resumption of blood flow to the breast; (d) detecting sounds generated by the resumption of blood flow to the breast; (e) repeating each of the steps (a)-(d) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

The compression surface may be a paddle, which is described more fully above. In some embodiments, such methods may further comprise securing a second compression device comprising an inflatable chamber to the paddle, and at least partially filling the inflatable chamber of the second compression device with a fluid, thereby compressing the first breast and the contralateral breast, respectively, between the inflatable chamber of the second compression device and the first compression device. In order to generate Korotkoff sounds, at least a portion of the fluid from the inflatable chamber of the first compression device, from the inflatable chamber of the second compression device, or both, may be released, and sounds that are generated by the resumption of blood flow to one or both breasts may be detected.

Also disclosed are methods comprising (a) securing a first compression device comprising an inflatable chamber to a compression paddle; (b) at least partially filling the inflatable chamber of the first compression device with a fluid, thereby compressing a first breast of a patient that is positioned on a support surface between the inflatable chamber and the support surface, and at least partially occluding blood flow to the breast; (c) releasing at least a portion of the fluid from the inflatable chamber, wherein the release of the fluid from the chamber controls the resumption of blood flow to the breast; (d) detecting sounds generated by the resumption of blood flow to the breast; (e) repeating each of steps (a)-(d) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

Such methods may further comprise securing a second compression device comprising an inflatable chamber over the support surface, and at least partially filling the inflatable chamber of the second compression device with a fluid, thereby compressing the first breast and the contralateral breast, respectively, between the inflatable chamber of the second compression device and the first compression device. In order to generate Korotkoff sounds, at least a portion of the fluid from the inflatable chamber of the first compression device, from the inflatable chamber of the second compression device, or both, may be released, and sounds that are generated by the resumption of blood flow to one or both breasts may be detected.

In another aspect, there are disclosed methods comprising (a) compressing a first breast of a patient, whereby the resulting compression occludes at least some blood flow to the breast; (b) at least partially relieving such compression, such that blood flow to the breast is at least partially restored; (c) detecting Korotkoff sounds within the breast; (d) repeating each of steps (a)-(c) with respect to the patient's contralateral breast; (f) comparing the detected sounds from the first breast, the contralateral breast, or both to comparable data from one or more subjects in which a disease or condition was known to be absent, known to be present, or both; and, (g) correlating the comparison to the presence or absence of the disease or condition in the patient, the stage of the disease or condition in the patient, or the response of the disease or condition in the patient to a therapy regimen.

Also disclosed are methods comprising using a comparison of data derived from the detection of Korotkoff sounds within a patient's first breast and data derived from the detection of Korotkoff sounds within a patient's contralateral breast to perform a diagnosis relating to the presence or absence of a disease or condition in the patient, the stage of the disease or condition in the patient, or the response of the disease or condition in the patient to a therapy regimen.

In accordance with any of the disclosed methods, the comparable data may be from a database comprising sound data. The methods may further comprise detecting sounds within the first breast and the contralateral breast when the breasts are not compressed. For example, sounds may be detected within the first breast and the contralateral breast prior to at least partially filling the inflatable chamber of the first compression device. Alternatively or additionally, sounds may be detected within the first breast and the contralateral breast following the release of fluid from the inflatable chamber of the first compression device and after blood flow to the respective breast (i.e., to the first and contralateral breast) has been substantially completely restored. Any of the sounds that are detected pursuant to the present methods may subsequently be used to form or contribute to a database of sounds, and/or may be compared to comparable data from one or more subjects in which a disease or condition was known to be absent, known to be present, or both, and such comparable data may be from a database comprising sound data. In other embodiments, the sounds that are detected from the first breast may be compared with the sounds from the contralateral breast. The comparison of the sounds from the first breast with the sounds from the contralateral breast may provide a comparison metric, and the metric may be used during an analysis of a database of sounds. Comparison metrics and the use thereof during an analysis of a database of sounds are described infra.

The instant methods can further comprise using a source of compressed air to inflate the chamber of any of the recited compression devices.

With respect to the present methods, the detection of sounds may be performed prior to compression of a patient's breast, during compression of a patient's breast, or following compression of a patient's breast. The detection of sounds within the breast may also be conducted at any stage of compression of the breast, i.e., when the breast is only partially compressed, or when the breast of fully compressed. When the sound detection step occurs at a specific stage during the instant methods with respect to a first breast, a sound detection step is preferably performed at the same stage in the contralateral breast so that appropriate data comparisons may be made if desired. When the methods involve the use of a compression device having an inflatable chamber, the detection of sounds within the breast may occur prior to at least partially filling the chamber of the compression device, when the chamber of the compression device has been at least partially filled, when the fluid introduced into the chamber of the compression device has been at least partially released from the chamber, when the fluid has been released from the chamber to the extent necessary to allow blood flow to the breast to be at least partially restored, or when the fluid has been released from the chamber to the extent necessary to allow blood flow to the breast to be substantially completely restored.

The detection of sounds generated by the resumption of blood flow to the breast may be conducted locally (i.e., at a portion or portions of the breast), or may be conducted over the entire breast ("globally"). If sound is detected locally, the portion(s) of the breast at which sound is detected may be a region of interest. A region of interest may be determined through reference to an image of the breast that was acquired prior to the sound-detection stage. For example, sound may be detected locally at a region of interest as identified through CAD methods. Once identified, the sound data retrieved from a region of interest within one breast may be compared with sound data that is retrieved from the corresponding anatomical location on the contralateral breast. The comparison can yield information regarding whether the region of interest is physiologically distinguishable from comparable tissue that is otherwise believed to be normal. Such findings may buttress the findings of the CAD program, and thereby alert the practitioner and/or warrant additional studies; alternatively, if the difference between the sound data from the first breast and the sound data from the contralateral breast is within a certain range of tolerance, then the practitioner could have reason to suspect that the region of interest as designated by the CAD program is not the region of a malignant growth.

In another embodiment, the methods can additionally comprise converting the detected sounds to an acceptable data format, such as a frequency domain signal. The converted sounds can be digitized for computer storage.

In another aspect of the present invention, provided are apparatuses comprising a support surface that is configured for accommodating a breast of a patient; a first compression device comprising an inflatable chamber, wherein the first compression device may be secured over a surface of the breast while positioned on the support surface, and wherein when the inflatable chamber is at least partially inflated by at least partially filling the inflatable chamber of the first compression device with a fluid, the breast is compressed between the inflatable chamber and the support surface and blood flow to the breast is at least partially occluded; and, a sound detector for detecting Korotkoff sounds that are generated within the breast when the compression of the breast is at least partially relieved, such that blood flow to the breast is at least partially restored.

Also disclosed are apparatuses comprising a support surface that is configured for accommodating a breast of a patient; a first compression device comprising an inflatable chamber that is secured to the support surface; a compression surface that may be positioned above a upper surface of the breast such that the breast is interposed between the first compression device and the compression surface; wherein when the inflatable chamber is at least partially inflated by at least partially filling the inflatable chamber of the first compression device with a fluid, the breast is compressed between the inflatable chamber and the compression surface and blood flow to the breast is at least partially occluded; and, a sound detector for detecting Korotkoff sounds that are generated within the breast when the compression of the breast is at least partially relieved, such that blood flow to the breast is at least partially restored.

The present apparatuses may further comprise a second compression device comprising an inflatable chamber that is secured to the compression surface, wherein when the inflatable chamber of the second compression device is at least partially filled with a fluid, the breast is compressed between the inflatable chamber of the second compression device and the first compression device. Thus, the breast may be compressed between the first compression device and the compression surface, and in certain embodiments, may in particular be compressed between the first compression device and a second compression device that is secured to the compression surface.

Also provided are apparatuses comprising a support surface that is configured for accommodating a breast of a patient; a compression surface that may be positioned above a upper surface of the breast such that said breast is interposed between the first compression device and the compression surface; a first compression device comprising an inflatable chamber that is secured to the compression surface, wherein when the inflatable chamber is at least partially inflated by at least partially filling the inflatable chamber of the first compression device with a fluid, the breast is compressed between the inflatable chamber and the support surface and blood flow to the breast is at least partially occluded; and, a sound detector for detecting Korotkoff sounds that are generated within the breast when the compression of the breast is at least partially relieved, such that blood flow to the breast is at least partially restored.

Pursuant to any of the disclosed methods and apparatuses, the sound detector may be adapted to generate an electrical signal that may be converted to a frequency domain signal. The sound detector may also be adapted to transfer the detected sound information to a sound converter that is configured to convert the detected sound information to a frequency domain signal.

Also provided are systems comprising any apparatus according the present disclosure and a database comprising sound data. Databases comprising sound data are also disclosed herein. The data within such databases correspond to a sound from at least one breast. Sound data may include Korotkoff sounds, sounds that are detected from within a breast that is not compressed and/or has not been compressed and released in order to produce Korotkoff sounds (e.g., has not been compressed and released within about one minute, about two minutes, about five minutes, about 10 minutes, or about 15 minutes or more prior to the detection of sounds from with the breast), or both. Preferably, the database comprises sound data from a plurality of breasts of different human subjects. For example, the database may include sound data from one or more subjects in which a disease or condition was known to be absent; sound data from one or more subjects in which a disease or condition was known to be present; sound data from one or more subjects in which a disease or condition was known to be present and at a particular stage of progression; sound data from one or more subjects in which a disease or condition was known to be present, wherein such subjects had undergone a therapy regimen (for example, for a previous occurrence of breast cancer, or for another condition, such as ductal carcinoma in situ (DCIS)); or any combination thereof. The data may be from subjects of particular ages, races, family histories, and the like, and preferably the database includes data from multiple subjects within a particular age group, race, family history category, and the like. The data may include sounds from a first breast of a subject and preferably also includes sounds from the contralateral breast of the subject. The data may comprise recordings of sounds (including Korotkoff sounds), recordings of one or more portions of each of one or more sounds, recordings of one or more characteristics of each of one or more sounds, and/or may comprise a graphical depiction of sounds, of one or more portions of sounds, or of one or more characteristics of sounds. When the data comprises a recording, the recording may be in digital or analog format. The instant database may also include an image of the breast from which sound data is present. The image may be a mammogram. When the database comprises sound data from a breast of a plurality of different subjects, the database may comprise at least one image of each of such breasts. The presence of both sound and image data in the database can be used to derive an understanding of the relationship between certain sounds and sound patterns from a breast and physical characteristics of that breast (e.g., characteristics of the vascularity of the breast), and/or can be used to conduct a more comprehensive comparison between the breast of a patient (and sound and/or image data therefrom) and comparable sound and/or image data from the database. For example, when, upon analysis of a database according to the present disclosure, particular sound data from a breast is found to correlate to a particular physical characteristic (such as a variety of abnormal vascularity) as depicted in an image of the breast, the detection of such sounds in a patient's breast can be used to predict whether the patient breast has the abnormal condition. Such predictions can be used to determine whether a more invasive or involved analysis of the breast is recommended, such as a biopsy and/or mammogram. The use of sound data can therefore be used for a predictive analysis before procedures that may be more complex, expensive, invasive, or uncomfortable are undertaken.

Referring now to the drawings wherein reference numerals refer to like elements, FIGS. 1A and 1B depict a view of a portion of apparatus 2 in accordance with an embodiment of the present invention having a support surface 4 for accommodating a breast of a patient. Support surface 4 may represent the upper portion of a stand or a wheeled platform. FIG. 1A depicts an embodiment wherein support surface 4 represents the upper portion of a stand. FIG. 1B depicts an embodiment wherein support surface 4 represents the upper portion of a wheeled platform that includes a set of wheels 6 for moving the wheeled platform from place to place. Handle 8 allows a user to angle the wheeled platform so that the weight of the wheeled platform rests entirely on wheels 6 when transportation of the wheeled platform is required, and to push, pull, or turn the wheeled platform to a desired location. When a wheeled platform is used, the wheels may be equipped with locking mechanisms to ensure that the platform remains stationary once it has been placed at a desired location. FIG. 1A depicts an embodiment featuring sound detectors 10 that are integrated with support surface 4, so that when a breast is at rest upon the support surface 4, the breast will be in acoustic communication with the sound detectors 10 and sounds can be detected from within the breast. In other embodiments, the sound detectors may include one or more sensors that may be taped to the outer surface of patient skin at particular locations on or near the breast, may be affixed proximate to the inflatable chamber of a compression device, or may be integrated with one or more other components of the present apparatuses. Support surface 4 may be equipped with one or more heating elements (not shown) in order to bring support surface 4 to a comfortable temperature for the patient.

FIG. 1C illustrates how an apparatus may be configured so that support surface 4 may be rotatable in either direction R or L about a center axis; support surface 4 may be affixed to a rotation mechanism 5, which allows the aforementioned rotation, while lock mechanism 7 may be used to fix support surface 4 in a particular position and thereby prevent additional rotation. Lock mechanism 7 may be activated or deactivated as desired in order to stop or permit the resumption of, respectively, the rotation of support surface 4. Mechanism 5 may also or alternatively be configured to allow tilting of support surface 4 relative to the floor (not shown). In such embodiments, support surface 4 may be tilted in any direction, such that the angle of support surface 4 relative to the floor is other than 180°. For example, it may be desirable to tilt a lengthwise edge of support surface 4 closer to the floor. Titling of the support surface can permit the breast to be placed in different positions relative to the floor for purposes of variable mammographic and/or sound analysis. FIG. 1C also illustrates a height-adjusting mechanism 9 that permits the adjustment of the height of support surface 4 relative to the ground; for example, it may be desired to adjust support surface 4 so that it is at a height that allows a seated or standing patient to comfortably place a breast thereon. Rotation mechanism 7 and/or height-adjusting mechanism 9 may be included in any embodiment of the present apparatuses.

FIG. 1D depicts an exemplary manner in which a first compression device 12 comprising an inflatable chamber 14 (shown using dashed lines) may be secured over a surface of a breast 16 of a patient positioned on support surface 4. Prior to the positioning of breast 16 on support surface 4, a protective or sanitary cover (not shown) may be positioned onto support surface 4. The protective or sanitary cover may be made from any appropriate material, such as, for example, cloth or paper, and may optionally be disposable. Crepe paper and non-woven fabric are commonly used on doctors' examining tables, and an appropriately sized portion of crepe paper that is optionally equipped with adhesive portions would adequately serve the purpose of providing a sanitary cover for support surface 4. The material for the protective or sanitary cover may also be chosen for patient comfort, for example, to minimize any feeling of cold from support surface 4. Inflatable chamber 14 of first compression device 12 may be at least partially filled with a fluid, thereby compressing breast 16 between inflatable chamber 14 and support surface 4 and at least partially occluding blood flow to the breast. Exemplary compression devices are depicted in FIGS. 3-6, and are described more fully below. Sounds may be detected from breast 16 at any time, for example, prior to securing the first compression device 12 over the breast, after securing the first compression device 12 over the breast but before filling the inflatable chamber 16 with fluid; while inflatable chamber 14 is being filled with fluid; after filling has ceased, while breast 16 is compressed; while compression of breast 16 is at least partially relieved, as blood flow at least partially resumes to breast 16; or any combination thereof.

Figure 2:
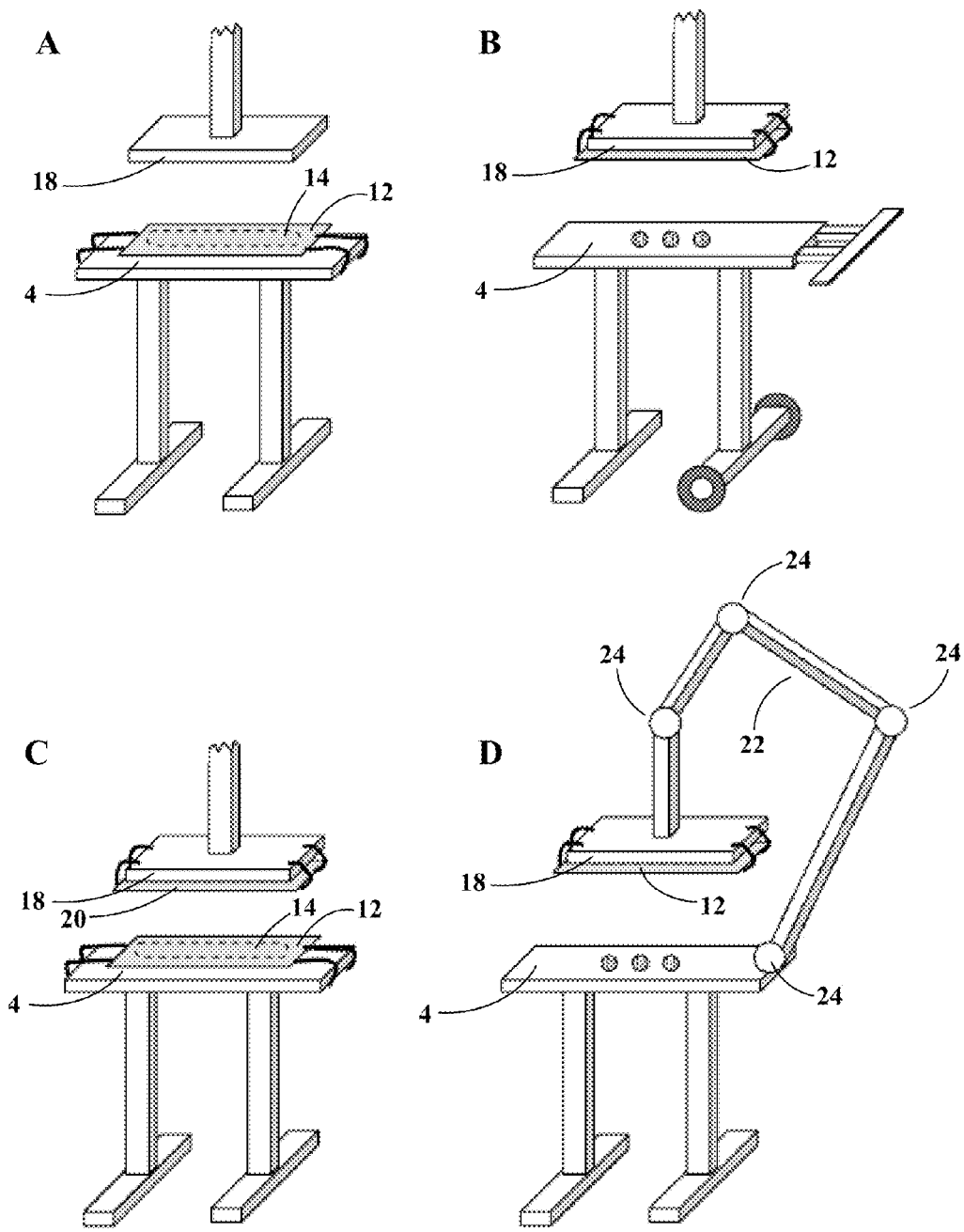
FIG. 2 shows exemplary embodiments of the present apparatuses that include a compression surface, so that when a breast of a subject is positioned upon the support surface, the breast is interposed between the support surface and the compression surface.
Figure 3:
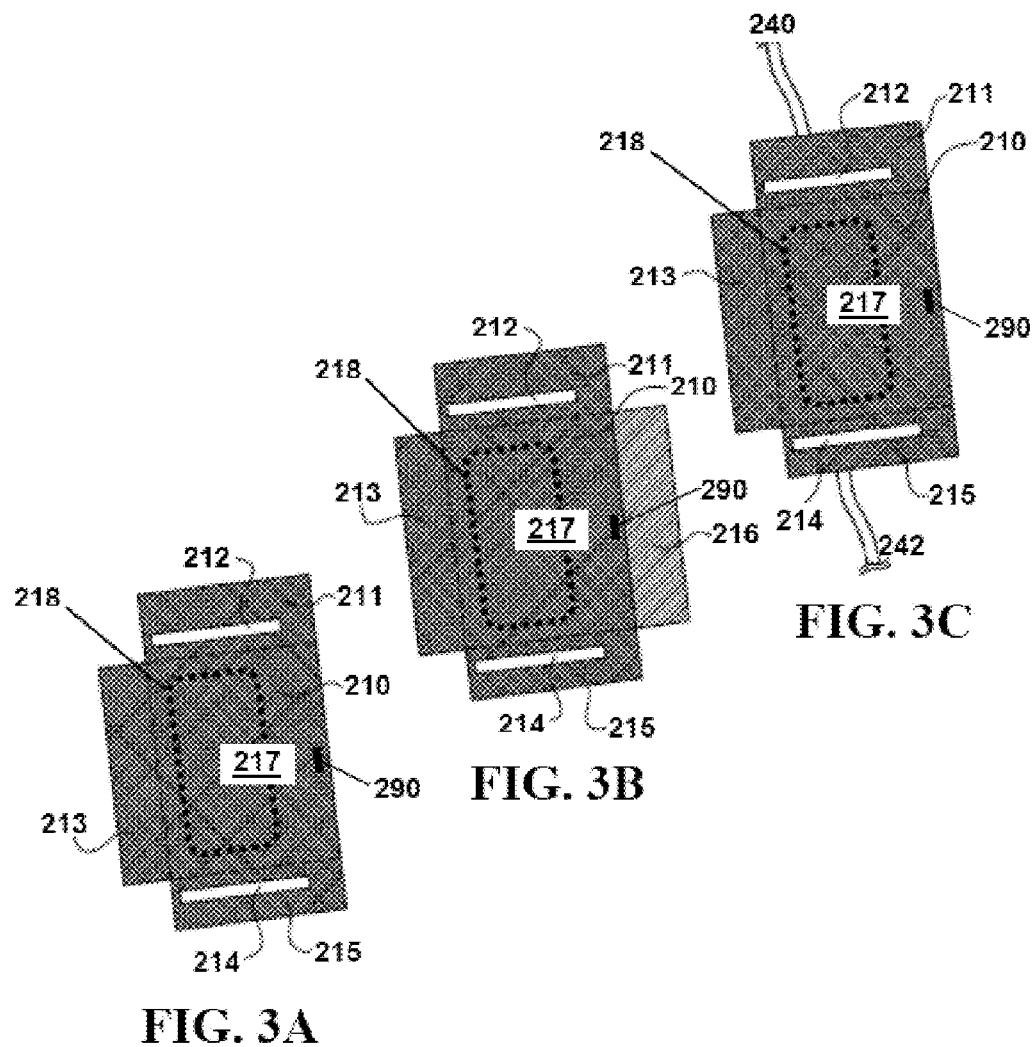
FIGS. 3A-3C each depict a top view of an embodiment of an exemplary compression device of the present invention.
Figure 6:
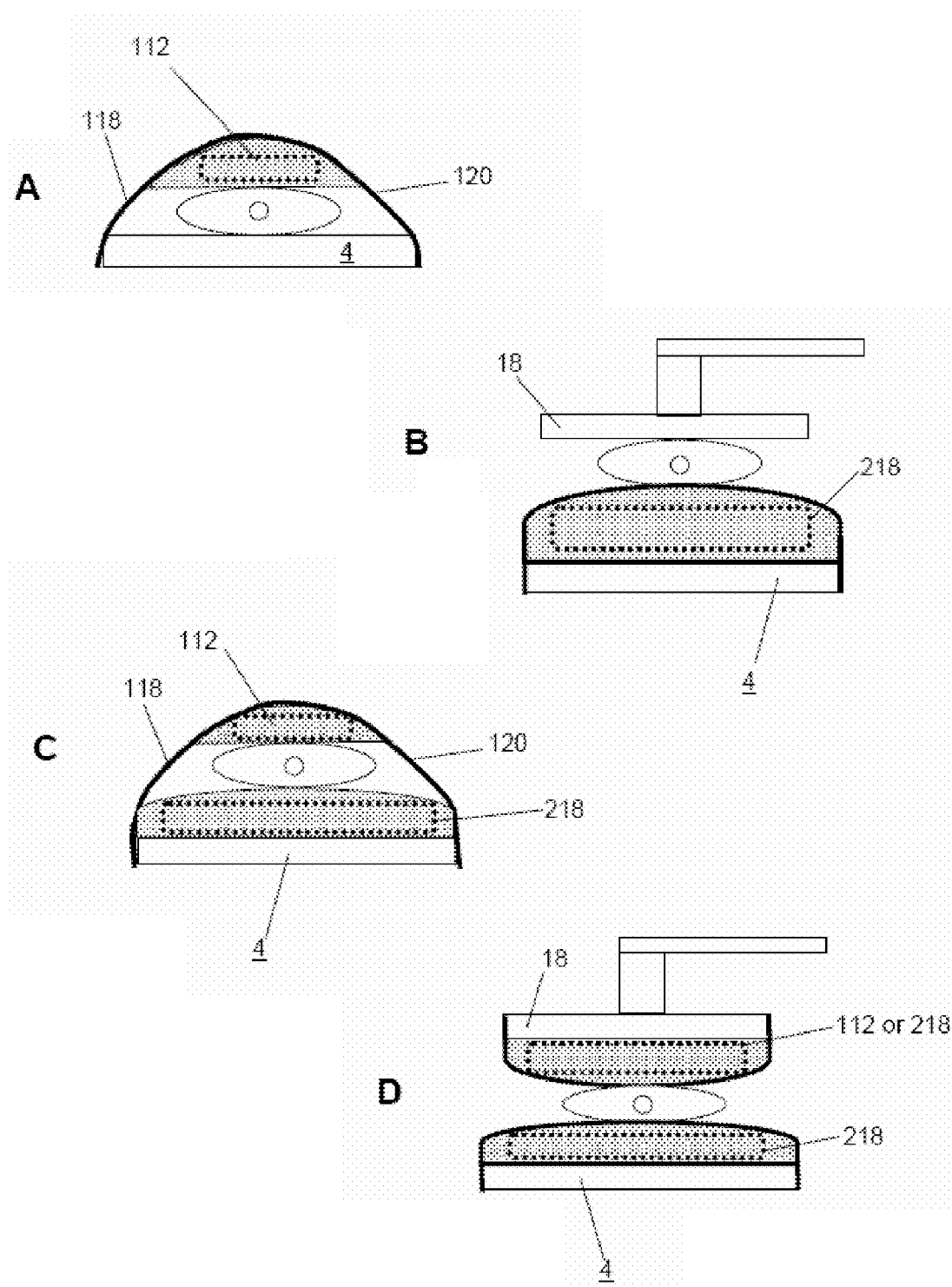
FIGS. 6A-6D depict front views of compression devices that are secured over the top of a breast to the support surface, secured directly over a support surface, secured both over the top of a breast and directly over a support surface, and secured both over a support surface and over a compression surface, respectively.

As shown in FIGS. 2A, 2B, and 2C, an apparatus according to the present invention may include a compression surface 18 that may be positioned above an upper surface of a breast that is positioned above support surface 4 of the apparatus.

In some embodiments, as illustrated in FIG. 2A, a first compression device 12 may be secured to support surface 4 so that when a breast of a subject (not shown) is positioned upon the support surface 4, the breast is interposed between the first compression device 12 and the compression surface 18. When the inflatable chamber 14 is at least partially filled with a fluid, the breast may be compressed between the inflatable chamber 14 and compression surface 18; such compression may at least partially occlude blood flow to the breast. Compression surface 18 may be movable in any direction relative to support surface 4; for example, compression surface 18 may be movable up and down relative to support surface 4 in order to bring the compression surface from a position away from a breast that is positioned upon support surface 4 and into contact with the upper surface of the breast prior to the filling of inflatable chamber 14 of first compression device 12; once compression surface 18 is in contact or very close to the upper surface of the breast, filling of inflatable chamber 14 will result in the compression of the breast between the first compression device 12 and compression surface 18, and the release of at least a portion of the fluid from inflatable chamber 14 will allow the resumption of blood flow to the breast.

FIG. 2D depicts an embodiment that features an exemplary way in which an apparatus in accordance with the present invention may be configured so that compression device 18 is movable relative to support surface 4. A jointed arm 22 may be affixed to both compression device 18 and support surface 4, and ball joints 24 may be included on arm 22 in order to allow the motion of each element of arm 22 to move in any direction. Manual force may be used to move arm 22 in order to position compression device 18, or arm 22 may be motorized so that mechanical controls (not shown) may be used to direct the positioning of compression device 18.

In other embodiments that include a compression device 18, illustrated in FIG. 2B, a first compression device 12 may be secured to compression device 18 so that when a breast of a subject (not shown) is positioned upon the support surface 4, the breast is interposed between the first compression device 12 and support surface 4. When the inflatable chamber of first compression device 12 is at least partially filled with a fluid, the breast may be compressed between the inflatable chamber (not shown) and support surface 4; such compression may at least partially occlude blood flow to the breast. Compression surface 18 may be movable in any direction relative to support surface 4; for example, compression surface 18 may be movable up and down relative to support surface 4 in order to bring the compression surface from a position away from a breast that is positioned upon support surface 4 and into contact with the upper surface of the breast prior to the filling of inflatable chamber of first compression device 12; once first compression device 12 is in contact or very close to the upper surface of the breast, filling of the inflatable chamber will result in the compression of the breast between the first compression device 12 and support surface 4, and the release of at least a portion of the fluid from the inflatable chamber will allow the resumption of blood flow to the breast.

In yet other embodiments that include a compression surface 18, as illustrated in FIG. 2C, a first compression device 12 may be secured to support surface 4, and a second compression device 20 may be secured to compression surface 18, so that when a breast of a subject (not shown) is positioned upon the support surface 4 via first compression device 12, the breast is interposed between the first compression device 12 and the second compression device 20. When the inflatable chamber of either or both of first compression device 12 or second compression device 20 are at least partially filled with a fluid, the breast may be compressed between first compression device 12 and second compression device 20; such compression may at least partially occlude blood flow to the breast. Compression surface 18 may be movable in any direction relative to support surface 4; for example, compression surface 18 may be movable up and down relative to support surface 4 in order to bring the compression surface from a position away from a breast that is positioned upon support surface 4 and into contact via second compression device 20 with the upper surface of the breast prior to the filling of the inflatable chamber of either or both of first compression device 12 or second compression device 20; once compression device 20 is in contact or very close to the upper surface of the breast, filling of inflatable chamber of either or both of first compression device 12 or second compression device 20 will result in the compression of the breast between the first compression device 12 and second compression device 20, and the release of at least a portion of the fluid from either or both of the inflatable chambers will allow the resumption of blood flow to the breast.

FIG. 3A is a top view of a compression device 217 in accordance with the invention that can be positioned over the support surface 4 and/or compression surface 18, i.e., beneath the breast when the breast is in position on the apparatus, and/or above the breast and secured beneath a compression surface 18. Compression device 217 is depicted with optional openings 212, 214, flattened, to show sections 210, 211, 213, and 215 for covering patient-contact surfaces of an apparatus. In one example, a compression device 217 is at least partly fabricated with a compressible material. Compressible material is preferably low Z elastic matrix material.

Compression device 217 is equipped with one or more inflatable chambers 218 having at least one manifold (not shown) that is operatively associated with each inflatable chamber, which can introduce compressed gas, for example, into the chamber 218 and/or receive compressed gas to vent it from the chamber 218. A source of fluid, for example, compressed air, enters one or more chambers 218 of the compression device 217 through a manifold (not shown). An optional second manifold can be operatively associated with the chamber 218 for venting or fluid inlet purposes.

In another example, as shown in FIG. 6B, the compression device of FIG. 6A is depicted with optional section 216 which is an extension of the compressible material that can be adapted with methods for retaining the compressible material in place on the support surface 4. Furthermore, there is no limitation on the material used to fabricate section 216. Optional section 216 can be integral with the compression device 217 or attached separately.

In yet a further example, as shown in FIG. 6C, the compression device of FIG. 6A is depicted with optional fasteners 240 and 242 which secure the device by wrapping around the underside of the support surface 4. One fastener is shown on each opposite side of the compression device, however, it is contemplated that multiple fasteners are suitable for attaching along either side. Furthermore, one fastener can be used which secures to an opposite side of the compression device. In another embodiment, the compression device depicted in FIG. 6C can be mounted over the top of compression surface 18. In this embodiment, only section 210 is preferably present, and the attached ends of fasteners 240, 242 can be affixed to section 210 of the device, the loose ends being used to secure the compression device to the compression surface, e.g., a paddle.

Fasteners can be straps that meet underneath the support surface or above the compression surface and tie together. In another example, fasteners can engage with each other using hook and loop fasteners. Yet another embodiment includes fasteners that can be one-piece elastic bands which are fixed to opposite sides of the compression device. The fasteners can be fabricated of any material suitable for fastening and unfastening. For ease of manufacture, however, it may be desirable to fabricate the fasteners out of the compressible material of the compression device. Fasteners can be integral with the compression device or compression surface, or may be attached separately.

In some embodiments, a cover substantially surrounds the inflatable chamber. In some instances, it may be desirable that the cover is compressible. In other instances, the cover is disposable. A combination of compressible and disposable covers can also be used. For example, in one embodiment, a cuff made of compressible material can have a pocket for holding a high pressure balloon where the cuff wraps around and/or releasably adheres to the breast and the support surface.

In one embodiment, the inflatable chamber has multiple chambers. In one example, a chamber is nested within the cavity of another chamber. Another example is a combination of chambers next to each other. The use of multiple chambers can be used to help distribute the compression force exerted against the breast. The shape of the chambers can vary as needed as well.

In evaluating equivocal areas of a breast it is sometimes desirable to provide a greater degree of compression in a localized area of a breast than can be achieved by uniform compression. This procedure, called spot compression, can be accomplished with the present invention by configuring at least one surface of the chamber with an area that expands to a greater degree than the surrounding surface, and positioning this area over the region of interest. Alternatively, a semi-rigid disc, e.g., plastic, can be placed on the breast over the region of interest before overlaying the breast with the compression device. As air is introduced into the chamber, the disc is pushed against the breast to exert additional compression force in the localized area. The discs can vary in size as needed. Identical episodes of spot compression may be separately performed with respect to each of a patient's breasts. Preferably, if a certain variation on compression is performed with respect to a first of a patient's breasts, then the same type of compression should be performed for purposes of the analysis of the second of the patient's breasts.

In FIG. 4A, depicting a side view of an embodiment of the present invention, a compression device is positioned over a patient's breast in contact with the support surface. In this embodiment, there are two side flaps 118 and 120 that secure the breast to the support surface 4. As shown in FIG. 5A, a free end of a first flap 130 can have a first fastener, 132. A second free end 138 can have a second fastener 140. The fasteners are optionally attachable or engagable with each other or individually to the bottom of the support surface. In another example, a flap is secured, either permanently or removably, to a portion of the support surface. Generally, when in position over the breast (and not inflated) as shown in FIG. 4, the one or more inflatable chambers 112 partially conform to the shape of the breast. Compressed air, for example, can be introduced, manually or automatically, to inflate the chamber 112.

FIG. 4B provides a side view of another embodiment of the present invention in which a first compression device 217 is positioned between a patient's breast and the support surface 4, in contact with the underside portion of the breast. There may be two side flaps 211 and 215 that secure the breast to the support surface 4. As shown in FIG. 5B, a free end of a first flap 211 can have a first fastener, 240. A free end of second flap 215 can have a second fastener 242. The fasteners are optionally attachable or engagable with each other or individually to the bottom of the support surface. Generally, when in position beneath the breast (and not inflated) as shown in FIGS. 4B & 5B, the inflatable chamber(s) 218 (internal—not shown) of the compression device 217 partially conforms to the shape of the breast. Compressed air, for example, can be introduced, manually or automatically, to inflate the chamber 218.

FIG. 4C provides a side view of yet another embodiment of the present invention in which a compression surface-mounted compression device 219 is provided. There may be two side flaps 221 and 223 that secure the breast to the compression surface 18. As shown in FIG. 5C, a free end of a first flap 221 can have a first fastener, 225. A free end of second flap 223 can have a second fastener 227. The fasteners are optionally attachable or engagable with each other or individually to the top of the compression surface 18. Generally, when in position on the underside of the compression surface 18 (and not inflated) as shown in FIGS. 4C & 5C, the inflatable chamber(s) (internal—not shown) of the compression surface-mounted compression device 219 partially conforms to the shape of the breast. Compressed air, for example, can be introduced, manually or automatically, to inflate the chamber.

As illustrated in FIG. 6A, when fluid is introduced into a chamber 112 of the first compression device, at least one surface of the chamber expands in the direction of the support surface 4. As the chamber expands, breast motion is limited and the breast is compressed against the support surface 4. Likewise, as depicted in FIG. 6B, when fluid is introduced into a chamber 218 of a compression device, at least one surface of the chamber expands in the direction of the compression surface 18 (which may be a paddle, for example), and as the chamber 218 expands, the breast is compressed against the compression surface 18. FIG. 6C provides an embodiment of the current invention in which both first and second compression devices are present, and wherein fluid has been introduced into chamber 112 of a compression device that is secured to the top of the breast and into chamber 218 of the compression device that is secured to the support surface 4 at the underside surface of the breast. The breast is compressed between the upper and lower devices by the expansion of chambers 112 and 218. FIG. 6D provides an embodiment of the current invention in which both a paddle-mounted compression device and a compression device that is secured to support surface 4 are present, and wherein fluid has been introduced into the inflatable chamber (112 or 218) of the compression device that is secured to the compression surface 18 and into the inflatable chamber 218 of the compression device on support surface 4. The breast is compressed between the two devices by the expansion of the chambers of the respective devices.

FIG. 7 depicts one possible arrangement among components that may be used to detect, store, and process sound information from within a patient's breast. A sound detector 250 is preferably placed in fluid communication with a breast, so that sounds may be faithfully transmitted therebetween. For example, the sound detector 250 may be affixed to the outer surface of the breast, or may be contacted with the inflatable chamber of a compression device in accordance with present invention. The sound information received by the detector 250 is transmitted to signal processor 260, which performs a conversion of the acoustical information received by the sound detector 250 into a frequency domain signal that is suitable for transfer by a computer 270. Computer 270 includes software for analyzing the data obtained from the signal processor 260. For example, the analysis software may include an algorithm that incorporates the sound data into a CAD program that uses the sound data and x-ray data to mark regions of interest on a mammogram. A recording device 280 stores the output of the computer software analysis and makes it available for retrieval, for example, by a radiologist or other clinician. Other software may be used to store the sound data, label it according to the profile of the patient from whose breast the data was derived, and organize it among other like data stored in database of sounds.

In accordance with one embodiment of the present invention (FIG. 8), the practitioner may refer to sound pattern data as collected by a sound detector and optionally optical density data (e.g., from a mammogram), results from an MRI, results from an ultrasound, or any combination thereof (step 311) in order to identify regions of interest within a patient's breast. Step 311 may additionally comprise comparing sound pattern data obtained from a first of a patient's breasts to the sound data obtained from the patient's contralateral breast. The comparison can yield information relating to the blood flow characteristics of the respective breasts, and can yield a comparison metric that can in turn be applied to the analysis of results in view of a database of sounds and optionally the mammogram, MRI, and/or ultrasound obtained at step 311. If the practitioner concludes that the region of interest represents normal tissue at step 321, no further action is taken. However, if the practitioner believes that the acoustic region of interest could represent cancerous growth at step 323, a recommendation will be made to conduct a biopsy 333 at the region of interest. It is anticipated that the number of unnecessary biopsies that are recommended by the practitioner will become attenuated through the use of the sound data parameter, optionally in combination with the optical density patterns present on the mammogram.

While the invention has been described and illustrated with reference to specific embodiments, those skilled in the art will recognize that modifications and variations may be made without departing from the principles of the invention as described herein and set forth in the following claims.

What is claimed:

1. A method comprising:
    (a) compressing a first breast of a patient in order to at least partially occlude blood flow to said breast;
    (b) at least partially relieving said compression, thereby allowing at least partial resumption of blood flow to the breast;
    (c) detecting sounds generated by the resumption of blood flow to the breast;
    (d) optionally repeating each of said steps (a)-(c) with respect to said patient's contralateral breast;
    (e) comparing said detected sounds from said first breast, said contralateral breast, or both to comparable data from one or more subjects in which a disease or condition was known to be absent, known to be present, or both; and, (f) correlating said comparison to the presence or absence of said disease or condition in said patient, the stage of said disease or condition in said patient, or the response of said disease or condition in said patient to a therapy regimen.

2. The method according to claim 1 wherein said comparable data is from a database comprising sound data.

3. The method according to claim 1 further comprising using said detected sounds to form or contribute to a database of sounds.

4. The method according to claim 1 wherein said patient is aged 40 years or younger.

5. The method according to claim 1 further comprising detecting sounds within said first breast and optionally said contralateral breast when said breasts are not compressed.

6. The method according to claim 5 comprising detecting sounds within said first breast and optionally said contralateral breast prior to step (a).

7. The method according to claim 5 comprising detecting sounds within said first breast and optionally said contralateral breast following said relieving of said compression and after blood flow to the respective breast has been substantially completely restored.

8. The method according to claim 1 further comprising comparing said detected sounds from said first breast with said detected sounds from said contralateral breast.

9. The method according to claim 8 wherein said comparison provides a comparison metric, and further comprising using said metric during an analysis of a database of sounds.

10. A method comprising:
(a) receiving sounds detected from at least one breast of a patient, wherein said sounds were detected by compressing said breast in order to at least partially occlude blood flow to said breast, at least partially relieving said compression, thereby allowing at least partial resumption of blood flow to said breast, and detecting sounds generated by the resumption of blood flow to said breast;
(b) comparing the received sounds to comparable data from one or more subjects in which a disease or condition was known to be absent, known to be present, or both; and,
(c) correlating said comparison to the presence or absence of said disease or condition in said patient, the stage of said disease or condition in said patient, or the response of said disease or condition in said patient to a therapy regimen.

11. The method according to claim 10 wherein said comparable data is from a database comprising sound data.

12. The method according to claim 10 further comprising using said detected sounds to form or contribute to a database of sounds.

13. The method according to claim 10 wherein said patient is aged 40 years or younger.

14. The method according to claim 10 further comprising comparing detected sounds from a first breast of said patient with detected sounds from the contralateral breast of said patient.

15. The method according to claim 14 wherein said comparison provides a comparison metric, and further comprising using said metric during an analysis of a database of sounds.

* * * * *